United States Patent [19]

Neurath et al.

[11] Patent Number: 4,540,573
[45] Date of Patent: Sep. 10, 1985

[54] UNDENATURED VIRUS-FREE BIOLOGICALLY ACTIVE PROTEIN DERIVATIVES

[75] Inventors: Alexander R. Neurath, New York; Bernard Horowitz, New Rochelle, both of N.Y.

[73] Assignee: New York Blood Center, Inc., New York, N.Y.

[21] Appl. No.: 514,375

[22] Filed: Jul. 14, 1983

[51] Int. Cl.$^3$ .................... A61K 39/00; A61K 35/14; A61K 37/00; C07G 7/00; C07C 103/52
[52] U.S. Cl. .................................. 424/85; 260/112 B; 260/112 R; 260/121; 260/112.5 R; 424/101; 514/2; 514/6
[58] Field of Search ............... 260/112 B, 112 R, 121; 424/85, 101, 89, 177

[56] References Cited

U.S. PATENT DOCUMENTS 3,962,421  6/1976  Neurath ................................ 424/89
4,314,997  2/1982  Shanbrom ........................... 424/101
4,315,919  2/1982  Shanbrom ........................... 424/177

OTHER PUBLICATIONS

Kirk–Othmer, *Encyclopedia of Chemical Technology*, vol. 4, 3rd Ed., Interscience Pub., 1978, pp. 25–61.
Ser. No. 368,250, Alfred Mayer Prince, filed 4-14-82.

*Primary Examiner*—Thomas G. Wiseman
*Assistant Examiner*—Robin Lyn Teskin
*Attorney, Agent, or Firm*—Sprung Horn Kramer & Woods

[57] ABSTRACT

A mammalian blood protein-containing composition such as whole blood, plasma, serum, plasma concentrate, cryoprecipitate, cryosupernatant, plasma fractionation precipitate or plasma fractionation supernatant substantially free of hepatitis and other lipid coated viruses with the yield of protein activity to total protein being at least 80% is disclosed. The protein-containing composition is contacted with di- or trialkylphosphate, preferably a mixture of trialkylphosphate and detergent, usually followed by removal of the di- or trialkylphosphate.

34 Claims, 8 Drawing Figures

REQUIREMENT FOR TWEEN 80 ADDITION TO TNBP

FIG. 5 — VSV: TNBP/TWEEN 80-0°C; TNBP ALONE - ROOM TEMPERATURE; TNBP/TWEEN - ROOM TEMPERATURE

FIG. 6 — SINDBIS: TNBP/TWEEN 80-°C; TNBP ALONE - ROOM TEMPERATURE; TNBP/TWEEN 80- ROOM TEMPERATURE

FIG. 7 — SENDAI: TNBP/TWEEN 80 -°C; TNBP ALONE - ROOM TEMPERATURE; TNBP/TWEEN 80- ROOM TEMPERATURE

FIG. 8 — EMC

○ TNBP/TWEEN 80-°C
● TNBP/TWEEN 80-ROOM TEMPERATURE
■ TNBP/TWEEN 80 ALONE-ROOM TEMPERATURE

UNDENATURED VIRUS-FREE BIOLOGICALLY ACTIVE PROTEIN DERIVATIVES

BACKGROUND OF THE INVENTION

1. Field of the Invention

This invention relates to undenatured virus-free biologically active protein-containing compositions. More especially, this invention relates to the inactivation of viruses, especially lipid coated viruses, e.g., hepatitis B in human blood, blood component, blood plasma or any fraction, concentrate or derivative thereof containing blood proteins non-blood sources including normal or cancer cells, the exudate from cancer or normal cells grown in culture, hybridomas, in products from gene splicing (DNA), etc., by use of di- or trialkyl phosphates, and to the resultant products. In particular, this invention relates to blood plasma or other plasma protein-containing compositions which are to be rendered substantially free of hepatitis B and/or non-A and non-B hepatitis or other viral infectivity, such blood plasma or fractions thereof having valuable labile proteins, such as, for example, factor VIII.

2. Discussion of Prior Art

Numerous attempts have been made to inactivate viruses such as hepatitis B virus (HBV) in mammalian, especially human, blood plasma. It is the practice in some countries to effect inactivation of the hepatitis B virus in the blood plasma by contacting the plasma with a viral inactivating agent of the type which crosslinks with the proteinaceous portion of hepatitis B virus, or which interacts with the nucleic acid of the virus. For instance, it is to attempt to inactivate hepatitis B virus by contact an aldehyde such as formaldehyde whereby crosslinking to the protein is effected and the hepatitis B virus is inactivated. It is also known to effect inactivation of the virus by contact with beta-propiolactone (BPL), an agent which acts on the nucleic acid of the virus. It is further known to use ultraviolet (UV) light, especially after a beta-propiolactone treatment.

Unfortunately, these agents often alter, denature or destroy valuable protein components especially so-called "labile" blood coagulation factors of the plasma under conditions required for effective inactivation of virus infectivity. For instance, in such inactivation procedures, factor VIII is inactivated or denatured to the extent of 50-90% or more of the factor VIII present in the untreated plasma. Because of the denaturing effects of these virus inactivating agents, it is necessary in the preparation of derivatives for administration to patients to concentrate large quantities of plasma so that the material to be administered to the patient once again has a sufficient concentration of the undenatured protein for effective therapeutic treatment. This concentration, however, does not affect reduction of the amount of denatured protein. As a result, the patient not only receives the undenatured protein but a quantity of denatured protein often many times that of the undenatured protein.

For instance, in the inactivation of hepatitis B virus in human blood plasma by beta-propiolactone, there is obtained as a result thereof, a plasma whose factor VIII has been 75% inactivated. The remaining 25% of the factor VIII is therefore present in such a small concentration, as a function of the plasma itself, that it is necessary to concentrate large quantities of the factor VIII to provide sufficient concentration to be of therapeutic value. Since such separation techniques do not efficiently remove denatured factor VIII from undenatured factor VIII, the material administered to the patent may contain more denatured protein than undenatured protein. Obviously, such inactivation is valuable from a standpoint of diminishing the risk of hepatitis virus infection. However, it requires the processing of large quantities of plasma and represents significant loss of valuable protein components. Furthermore, administration of large amounts of denatured proteins may render these antigenic to the host and thus give rise to autoimmune diseases, or perhaps, rheumatoid arthritis.

The loss of these valuable protein components is not limited to factor VIII, one of the most labile of the valuable proteins in mammalian blood plasma. Similar protein denaturation is experienced in respect of the following other valuable plasma components: coagulation factors II, VII, IX, X; plasmin, fibrinogen (factor I) IgM, hemoglobin, interferon, etc.

Factor VIII, however, is denatured to a larger extent than many of the other valuable proteins present in blood plasma.

As a result of the foregoing, except in the processing of serum albumin, a stable plasma protein solution which can withstand pasteurization, it is largely the practice in the United States in respect of the processing of blood proteins to take no step in respect of the sterilization for inactivation of viruses. As a result, recipients of factor VIII, gamma-globulin, factor IX, fibrinogen, etc., must accept the risk that the valuable protein components being administered may be contaminated with hepatitis viruses as well as other infectious viruses. As a result, these recipients face the danger of becoming infected by these viruses and having to endure the damage which the virus causes to the liver and other organ systems and consequent incapacitation and illness which may lead to death.

The BPL/UV inactivation procedure discussed above has not so far been adopted in the United States for numerous reasons, one of which lies in the fact that many researchers believe that BPL is itself deleterious since it cannot be removed completely following the inactivation and thus may remain in plasma and plasma derivatives. BPL has been shown to be carcinogenic in animals and is dangerous even to personnel handling it.

Other methods for the inactivation of hepatitis B virus in the plasma are known, but are usually impractical. One method involves the addition of antibodies to the plasma whereby an immune complex is formed. The expense of antibody formation and purification add significantly to the cost of the plasma production; furthermore, there is no assurance that a sufficient quantity of hepatitis B or non-A, non-B virus is inactivated. There is currently no test for non-A, non-B antibodies (although there is a test for the virus); hence, it is not possible to select plasma containing high titers of anti non-A, non-B antibody.

It is to be understood that the problems of inactivation of the viruses in plasma are distinct from the problems of inactivation of the viruses themselves due to the copresence of the desirable proteinaceous components of the plasma. Thus, while it is known how to inactivate the hepatitis B virus, crosslinking agents, for example, glutaraldehyde, nucleic acid reacting chemicals, for example BPL or formaldehyde, or oxidizing agents, for example chlorox, etc., it has been believed that these methods are not suitable for the inactivation of the virus in plasma due to the observation that most of these activating agents (sodium hypochlorite, formaldehyde, beta-propiolactone) denatured the valuable proteinaceous components of the plasma.

U.S. Pat. No. 4,315,919 to Shanbrom describes a method of depyrogenating a proteinaceous biological or pharmaceutical product by contacting such proteinaceous product with a non-denaturing amphiphile.

U.S. Pat. No. 4,314,997 to Shanbrom describes a method of reducing pyrogenicity, hepatitis infectivity and clotting activation of a plasma protein product by contacting the product with a non-denatured amphiphile.

Both Shanbrom '919 and '997 contemplate the use of a non-ionic detergent, for example, "Tween 80" as the amphiphile. It will be shown hereinafter that treatment with "Tween 80" by itself is relatively ineffective as a viral inactivating agent.

U.S. Pat. No. 3,962,421 describes a method for the disruption of infectious lipid-containing viruses for preparing sub-unit vaccines by contacting the virus in an aqueous medium with a wetting agent and a trialkylphosphate. Such aqueous medium is defined as allantonic fluid, tissue culture fluid, aqueous extract or suspension of central nervous system tissue, blood cell eluate and an aqueous extract or suspension of fowl embryo. The patent does not describe hepatitis, nor is it concerned with preparation of blood derivatives containing labile blood protein substantially free of viral infectivity. It is only concerned with disrupting the envelope of lipid containing viruses for the production of vaccines and not with avoiding or reducing protein denaturation en route to a blood derivative.

Problems may also exist in deriving valuable proteins from non-blood sources. These sources include, but are not limited to, mammalian milk, ascitic fluid, saliva, placental extracts, tissue culture cell lines and their extracts including transformed cells, and products of fermentation. For instance, the human lymphoblastoid cells have been isolated which produce alpha interferon. However, the cell line in commercial use today contains Epstein-Barr virus genes. It has been a major concern that the use of interferon produced by these cells would transmit viral infection or induce viral caused cancerous growth.

The present invention is directed to achieving three goals, namely, (1) a safe, (2) viral inactivated protein-containing composition, (3) without incurring substantial protein denaturation. As shown above these three goals are not necessarily compatible since, for example beta-propiolactone inactivates viral infectivity, but is unsafe and substances such as formaldehyde inactivate viruses, but also substantially denature the valuable plasma proteins, for example, factor VIII.

It, therefore, became desirable to provide a process for obtaining protein-containing compositions which does not substantially denature the valuable protein components therein and which does not entail the use of a proven carcinogenic agent. More especially, it is desirable to provide blood protein-containing compositions in which substantially all of the hepatitis viruses and other viruses present are inactivated and in which denatured protein such as factor VIII account for only a small amount of the total amount of these proteins in the blood protein-containing composition.

It is a further object to provide products from cancer or normal cells or from fermentation processes following gene insertion which are substantially free of virus, especially lipid-containing viruses.

SUMMARY OF THE INVENTION

It has now been discovered, quite surprisingly, that while most of the viral inactivating agents denature factor VIII and other valuable blood plasma proteins, that not all viral inactivating agents have such effect. It has been discovered that a protein-containing composition such as whole blood, blood cell proteins, blood plasma, a blood plasma fractionation precipitate, a blood plasma fractionation supernatant, cryoprecipitate, cryosupernatant, or portion or derivative thereof or serum or a non-blood product produced from normal or cancerous cells (e.g. via recombinant DNA technology) is contacted for a sufficient period of time with a dialkylphosphate or a trialkylphosphate that lipid containing viruses such as the hepatitis viruses present in the composition are virtually entirely inactivated without substantial denaturation of proteins therein. By contacting blood protein mixture or concentrate thereof or fraction thereof with a di-or trialkylphosphate, followed by removal of the di- or trialkylphosphate, hepatitis viruses can be substantially inactivated, e.g., to an inactivation of greater than 4 logs, while realizing a yield of protein activity to total protein of at least 80%.

By such procedures there is provided a blood protein-containing composition such as mammalian whole blood, blood cell derivatives (e.g., hemoglobin, alpha-interferon, T-cell growth factor, platelet-derived growth factor, etc.), plasminogen activator, blood plasma, blood plasma fraction, blood plasma precipitate (e.g., cryoprecipitate, ethanol precipitate or polyethylene glycol precipitate), or supernatant (e.g., cryosupernatant, ethanol supernatant or polyethylene glycol supernatant), characterized by the presence of one or more blood proteins such as labile blood factor VIII having a total yield of protein activity to total protein of at least 80%, preferably at least 85%, more preferably 95% and most preferably 98% to 100%, said blood protein-containing composition having greatly reduced or virtually no hepatitis viruses. Virus in a serum is determined by infectivity titrations.

By the inactivation procedure of the invention, most if not virtually all of the hepatitis viruses contained therein would be inactivated. The method for determining infectivity levels by in vivo chimpanzees is discussed by Prince, A. M., Stephen, W., Brotman, B. and van den Ende, M. C., "Evaluation of the Effect of Beta-propiolactone/Ultraviolet Irradiation (BPL/UV) Treatment of Source Plasma on Hepatitis Transmission by factor IX Complex in Chimpanzees, Thrombosis and Haemostasis", 44: 138-142, 1980.

The hepatitis virus is inactivated by treatment with the di- or trialkylphosphate described herein, and is not inactivated because of inclusion in the plasma of antibodies which bind with the hepatitis viruses and form immune complexes.

Inactivation of virus is obtained to the extent of at least "4 logs", i.e., virus in a serum is totally inactivated to the extent determined by infectivity studies where that virus is present in the untreated serum in such a concentration that even after dilution to $10^4$, viral activity can be measured.

BRIEF DESCRIPTION OF THE DRAWINGS

FIG. 5 is a plot of log titer value versus hours for VSV virus for TNBP/Tween 80 at 0° C. and at room temperature and TNBP alone (at room temperature);

FIG. 6 is a plot of log titer value versus hours for Sindbis virus for TNBP/Tween 80 at 0° C. and at room temperature and TNBP alone (at room temperature);

FIG. 7 is a plot of log titer value versus hours for Sendai virus for TNBP /Tween 80 at 0° C. and at room temperature and TNBP alone (at room temperature); and FIG. 8 is a plot of log titer value versus hours for EMC virus for TNBP/Tween 80 at 0° C. and at room temperature and TNBP alone (at room temperature).

Figure 1:
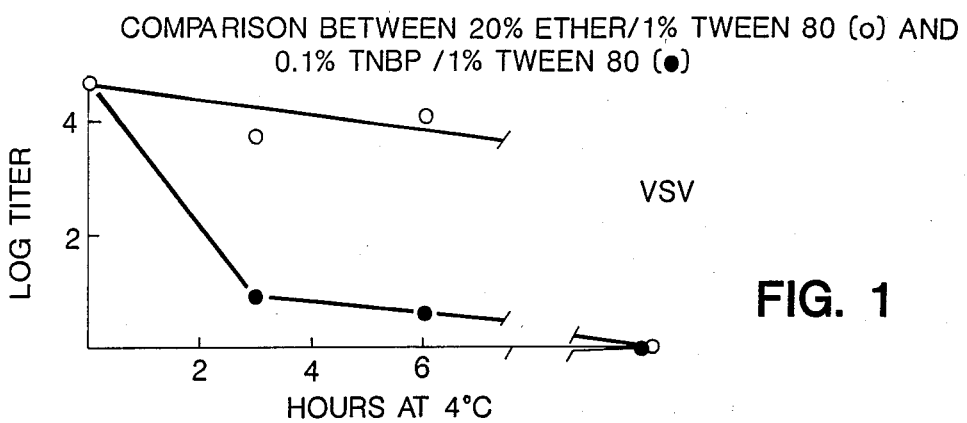
FIG. 1 shows virus inactivation as a function of log titer value versus time for VSV virus (vesicular stomatitis virus) treated according to the present invention and treated with ether/Tween 80. The lower log titer for treatment according to the present invention indicates greater virus inactivation.

The Sindbis, Sendai and VSV viruses are typical lipid containing viruses and are used herein to determine the effect of di- or trialkylphosphate on lipid coated viruses generally.

DETAILED DESCRIPTION OF THE INVENTION

Blood is made up of solids (cells, i.e., erythrocytes, leucocytes, and thrombocytes) and liquid (plasma). The cells contain potentially valuable substances such as hemoglobin, and they can be induced to make other potentially valuable substances such as interferons, growth factors, and other biological response modifiers. The plasma is composed mainly of water, salts, lipids and proteins. The proteins are divided into groups called fibrinogens, serum globulins and serum albumins. Typical antibodies (immune globulins) found in human blood plasma include those directed against infectious hepatitis, influenza H, etc.

Blood transfusions are used to treat anemia resulting from disease or hemorrhage, shock resulting from loss of plasma proteins or loss of circulating volume, diseases where an adequate level of plasma protein is not maintained, for example, hemophilia, and to bestow passive immunization.

Whole blood must be carefully typed and cross matched prior to administration. Plasma, however, does not require prior testing. For certain applications, only a proper fraction of the plasma is required, such as factor VIII for treatment of hemophilia or von Willebrand's disease.

With certain diseases one or several of the components of blood may be lacking. Thus the administration of the proper fraction will suffice, and the other components will not be "wasted" on the patient; the other fractions can be used for another patient. The separation of blood into components and their subsequent fractionation allows the proteins to be concentrated, thus permitting concentrates to be treated. Of great importance, too, is the fact that the plasma fractions can be stored for much longer periods than whole blood and they can be distributed in the liquid, the frozen, or the dried state. Finally, it allows salvaging from blood banks the plasma portions of outdated whole blood that are unsafe for administration as whole blood.

Proteins found in human plasma include prealbumin, retinol-binding protein, albumin, alpha-globulins, beta-globulins, gamma-globulins (immune serum globulins), the coagulation proteins (antithrombin III, prothrombin, plasminogen, antiemophilic factor-factor VIII, fibrin-stabilizing factor-factor XIII, fibrinogen), immunoglobins(immunoglobulins G, A, M, D, and E), and the complement components. There are currently more than 100 plasma proteins that have been described. A comprehensive listing can be found in "The Plasma Proteins", ed. Putnam, F. W., Academic Press, New York (1975).

Proteins found in the blood cell fraction include hemoglobin, fibronectin, fibrinogen, enzymes of carbohydrate and protein metabolism, etc. In addition, the synthesis of other proteins can be induced, such as interferons and growth factors A comprehensive list of inducible leukocyte proteins can be found in Stanley Cohen, Edgar Pick, J. J. Oppenheim, "Biology of the Lymphokines", Academic Press, N.Y. (1979).

Blood plasma fractionation generally involves the use of organic solvents such as ethanol, ether and polyethylene glycol at low temperatures and at controlled pH values to effect precipitation of a particular fraction containing one or more plasma proteins. The resultant supernatant can itself then be precipitated and so on until the desired degree of fractionation is attained. More recently, separations are based on chromatographic processes. An excellent survey of blood fractionation appears in *Kirk-Othmer's Encylopedia of Chemical Technology*, Third Edition, Interscience Publishers, Volume 4, pages 25 to 62, the entire contents of which are incorporated by reference herein.

The major components of a cold ethanol fractionation are as follows:

| Fraction | Proteins |
| --- | --- |
| I | fibrinogen; cold insoluble globulin; factor VIII; properdin |
| II and III | IgG; IgM; IgA; fibrinogen; beta-lipoprotein; prothrombin; plasminogen; plasmin inhibitor; factor V; factor VII; factor IX; factor X; thrombin; antithrombin; isoagglutinins; cerutoplasmin; complement C'1, C'3 |
| IV-1 | alpha$_1$-lipoprotein, cerutoplasmin, plasmininhibitor; factor IX; peptidase; alpha-and-beta-globulins |
| IV-4 | transferrin; thyroxine binding globulin; serum esterase; alpha$_1$-lipoprotein; albumin; alkaline phosphatase |
| V | albumin; alpha-globulin |
| VI | alpha$_1$-acid glycoprotein; albumin |

The above fractionation scheme can serve as a basis for further fractionations. Fraction II and III, for example, can be further fractionated to obtain immune serum globulin (ISG).

Another fractionation scheme involves use of frozen plasma which is thawed into a cryoprecipitate containing AHF (antihemophilic factor) and fibronectin and a cryosupernatant. The cryoprecipitate is then fractionated into fibronectin and AHF.

Polyethylene glycol has been used to prepare high purity AHF and non-aggregated ISG.

High risk products with respect to the transmission of hepatitis B and non-A, non-B are fibrinogen, AHF and prothrombin complex, and all other blood protein preparations except immune serum globulin and, because they are pasteurized, albumin solutions. Hepatitis tests presently available can indicate the presence of hepatitis B surface antigen, but there is presently no screening test for non-A, non-B hepatitis.

The present invention is directed to contacting with di- or trialkylphosphate a blood protein-containing composition such as whole mammalian blood, blood cells thereof, blood cell proteins, blood plasma thereof, precipitate from any fractionation of such plasma, supernatant from any fractionation of such plasma, cryoprecipitate cryosupernatant or any portions or derivatives of the above that contain blood proteins such as, for example, prothrombin complex (factors II, VII IX and X) and cryoprecipitate (factors I and VIII). The present invention is also concerned with contacting di- or trialkylphosphate with a serum containing one or more blood proteins. Furthermore, the present invention is directed to contacting di- or trialkylphosphate with a blood protein-containing fraction containing at least one blood protein such as the following: factor II, factor VII, factor VIII, factor IX, factor X, fibrinogen and IgM. Additionally, the present invention concerns contacting a cell lysate or proteins induced in blood cells with di- or trialkylphosphate.

Such blood protein-containing composition is contacted with a dialkylphosphate or a trialkylphosphate having alkyl groups which contain 1 to 10 carbon atoms, especially 2 to 10 carbon atoms. Illustrative members of trialkylphosphates for use in the present invention include tri-(n-butyl) phosphate, tri-(t-butyl) phosphate, tri-(n-hexyl) phosphate, tri-(2-ethylhexyl) phosphate, tri-(n-decyl) phosphate, just to name a few. An especially preferred trialkylphosphate is tri-(n-butyl) phosphate. Mixtures of different trialkylphosphates can also be employed as well as phosphates having alkyl groups of different alkyl chains, for example, ethyl, di(n-butyl) phosphate. Similarly, the respective dialkylphosphates can be employed including those of different alkyl group mixtures of dialkylphosphate. Furthermore, mixtures of di- and trialkylphosphates can be employed.

Di- or trialkylphosphates for use in the present invention are employed in an amount between about 0.01 mg/ml and about 100 mg/ml, and preferably between about 0.1 mg/ml and about 10 mg/ml.

The di- or trialkylphosphate can be used with or without the addition of wetting agents. It is preferred, however, to use di- or trialkylphosphate in conjunction with a wetting agent. Such wetting agent can be added either before, simultaneously with or after the di- or trialkylphosphate contacts the blood protein-containing composition. The function of the wetting agent is to enhance the contact of the virus in the blood protein-containing composition with the di- or trialkylphosphate. The wetting agent alone does not adequately inactivate the virus.

Preferred wetting agents are non-toxic detergents. Contemplated nonionic detergents include those which disperse at the prevailing temperature at least 0.1% by weight of the fat in an aqueous solution containing the same when 1 gram detergent per 100 ml of solution is introduced therein. In particular there is contemplated detergents which include polyoxyethylene derivatives of fatty acids, partial esters of sorbitol anhydrides, for example, those products known commercially as "Tween 80", "Tween 20" and "polysorbate 80" and nonionic oil soluble water detergents such as that sold commercially under the trademark "Triton X 100" (oxyethylated alkylphenol). Also contemplated is sodium deoxycholate as well as the "Zwittergents" which are synthetic zwitterionic detergents known as "sulfobetaines" such as N-dodecyl-N, N-dimethyl-2-ammonio-1 ethane sulphonate and its congeners or nonionic detergents such as octyl-beta-D-glucopyranoside.

Substances which might enhance the effectiveness of alkylphosphates include reducing agents such as mercaptoethanol, dithiothreitol, dithioerythritol, and dithiooctanoic acid. Suitable nonionic surfactants are oxyethylated alkyl phenols, polyoxyethylene sorbitan fatty acid esters, polyoxyethylene acids, polyoxyethylene alcohols, polyoxyethylene oils and polyoxyethylene oxypropylene fatty acids. Some specific examples are the following:

alkylphenoxypolyethoxy (30) ethanol
polyoxyethylene(2) sorbitan monolaurate
polyoxyethylene (20) sorbitan monopalmitate
polyoxyethylene (20) sorbitan monostearate
polyoxyethylene (20) sorbitan tristearate
polyoxyethylene (20) sorbitan monooleate
polyoxyethylene (20) sorbitan trioleate
polyoxyethylene (20) palmitate
polyoxyethylene (20) lauryl ether
polyoxyethylene (20)cetyl ether
polyoxyethylene (20) stearyl ether
polyoxyethylene (20) oleyl ether
polyoxyethylene (25) hydrogenated castor oil
polyoxyethylene (25) oxypropylene monostearate The amount of wetting agent, if employed, is not crucial, for example, from about 0.001% to about 10%, preferably about 0.01 to 1.5%, can be used.

Di- and trialkylphosphates may be used in conjunction with other inactivating agents such as alcohol or ethers with or without the copresence of wetting agents in accordance with copending application Ser. No. 368,250 entitled "Sterilized Plasma and Plasma Derivatives and Process Therefor", assigned to the assignee hereof.

The ether or alcohol can be added in an amount of 1 to 50%, preferably 5 to 25% by weight, based on the volume of blood plasma, or concentrate or other blood plasma protein-containing composition to be treated.

Particularly contemplated ethers for inactivation use in accordance with the invention are those having the formula $$R^1-O-R^2$$

wherein $R^1$ and $R^2$ are independently $C_1-C_{18}$ alkyl or alkenyl which can contain an O or S atom in the chain, preferably $C_1-C_8$ alkyl or alkenyl. Especially contemplated ethers are dimethyl ether, diethyl ether, ethyl propyl ether, methyl-butyl ether, methyl isopropyl ether and methyl isobutyl ether.

Alcohols contemplated include those of the formula $$R^3OH$$

wherein $R^3$ is a $C_1$ to $C_{18}$ alkyl or alkenyl radical which can contain one or more oxygen or sulfur atoms in the chain and which can be substituted by one or more hydroxyl groups.

Especially contemplated alcohols are those where the alkyl or alkenyl group is between 1 and 8 atoms. Particularly contemplated alcohols include methanol, ethanol, propanol, isopropanol, n-butanol, isobutanol, n-pentanol and the isopentanols. Also contemplated are compounds such as ethylene glycol, 1,2-propylene glycol, 1,3-propane diol, 1,4-butanediol, 2-hydroxy isobutanol (2-methy, 1,2-dihydroxypropane).

Treatment of blood protein-containing compositions with trialkylphosphate is effected at a temperature between $-5°$ C. and 70°, preferably between 0° C. and 60° C. The time of such treatment (contact) is for at least 1 minute, preferably at least 1 hour and generally 4 to 24 hours. The treatment is normally effective at atmospheric pressure, although subatmospheric and superatmospheric pressures can also be employed.

Normally, after the treatment, the trialkylphosphate and other inactivating agents, for example, ether, are removed, although such is not necessary in all instances, depending upon the nature of the virus inactivating agents and the intended further processing of the blood plasma protein-containing composition.

To remove ether from plasma the plasma is generally subjected to a temperature of 4° C. to 37° C. with a slight vacuum imposed to draw off residual ether. Preferably means are provided to spread the plasma as a thin film to insure maximum contact and removal of the ether. Other methods for removal of ether in activating agents include:

(1) bubbling of nitrogen gas;
(2) diafiltration using ether insoluble, e.g. "TEFLON", microporous membranes which retain the plasma proteins;
(3) absorption of desired plasma components on chromatographic or affinity chromographic supports;
(4) precipitation, for example, by salting out of plasma proteins;
(5) lyophilization, etc.

When alcohol or nonionic detergents are employed with the trialkylphosphate they are removed by (2) to (5) above.

Di- or trialkylphosphate can be removed as follows:
(a) Removal from AHF can be effected by precipitation of AHF with 2.2 molal glycine and 2.0M sodium chloride
(b) Removal from fibronectin can be effected by binding the fibronectin on a column of insolubilized gelatin and washing the bound fibronectin free of reagent.

Generally speaking, any ether present is initially removed prior to removal of any detergent. The ether may be recovered for reuse by the use of suitable distillation/condenser systems well known to the art.

Alcohol is normally removed together with detergent. If the detergent includes both alcohol and ether, the ether is normally removed before the alcohol.

The process of the invention can be combined with still other modes of inactivating viruses including those for non-lipid coated viruses. For instance, a heating step can be effected in the presence of a protein stabilizer, e.g., an agent which stabilizes the labile protein (AHF) against inactivation by heat. Moreover, the heating can be carried out using stabilizers which also tend to protect all protein, including components of the virus, against heat if the heating is carried out for a sufficient length of time, e.g., at least 5 hours and preferably at least 10 hours at a temperature of 50°–70° C., especially 60° C. By such mode the virus is preferentially inactivated, nevertheless, while the protein retains a substantial amount, e.g., $\geqq 80\%$ of its protein activity. Of course, the best treatment can also be carried out simultaneously with the alkyl phosphate treatment.

The treatment of plasma or its concentrates, fractions or derivatives in accordance with the present invention can be effected using di- or trialkylphosphate immobilized on a solid substrate. The same can be fixed to a macro-molecular structure such as one of the type used as a backbone for ion exchange reactions, thereby permitting easy removal of the trialkylphosphate from the plasma or plasma concentrate. Alternatively the phosphate can be insolubilized and immobilized on a solid support such as glass beads, etc., using silane or siloxane coupling agents.

The method of the present invention permits the pooling of human blood plasma and the treatment of the pooled human blood plasma in the form of such pooled plasma. It also permits the realization of blood product derivatives such as factor VIII, gamma globulin, factor IX or the prothrombin complex (factors II, VII, IX, X), fibrinogen and any other blood derivative including HBsAg used for the preparation of HBV vaccine, all of which contain little or no residual infective hepatitis or other viruses.

The present invention is directed, inter alia, to producing a blood plasma protein-containing composition such as blood, blood plasma, blood plasma fractions, etc., which is substantially free of infectious virus, yet which contains a substantial amount of viable (undenatured) protein. More particularly, the present invention is directed to inactivation of lipid-containing virus and preferentially inactivation of hepatitis B and non-B, non-A virus. Other viruses inactivated by the present invention include, for example, cytomegaloviruses, Epstein Barr viruses, lactic dehydrogenase viruses, herpes group viruses, rhabdoviruses, leukoviruses, myxoviruses, alphaviruses, Arboviruses (group B), paramyxoviruses, arenaviruses, and coronaviruses.

According to the present invention, there is contemplated a protein-containing composition—a product produced from normal or cancerous cells or by normal or cancerous cells (e.g., via recombinant DNA technology), such as mammalian blood, blood plasma, blood plasma fractions, precipitates from blood fractionation and supernatants from blood fractionation having an extent of inactivation of virus greater than 4 logs of virus such as hepatitis B and non-A, non-B, and having a yield of protein activity to total protein of at least 80%, preferably at least 95% and most preferably 98% to 100%.

Further contemplated by the present invention is a composition containing factor VIII which is substantially free of hepatitis virus to the extent of having an inactivation of greater than 4 logs of the virus and a yield of protein activity to total protein of at least 80%, preferably at least 85%, more preferably at least 95% and most preferably 98% to 100%.

The process of the present invention has been described in terms of treatment of plasma, plasma fractions, plasma concentrates or components thereof. The process, however, is also useful in treating the solid components of blood, lysates or proteins secreted by cells. Thus, also contemplated are treatment of platelet concentrates, white cell (leukocyte) concentrates, and leukocyte-poor packed red cells as well as platelet rich plasma, platelet concentrates and platelet poor plasma including packed cell masses comprising the white buffy coat consisting of white blood cells above packed red cells. Also contemplated is the treatment of masses containing concentrates of granulocytes, monocytes, interferon, and transfer factor.

One can treat plasma itself according to the present invention or fresh frozen plasma, thawed frozen plasma, cryoprecipitate, cryosupernatants or concentrates from frozen plasma as well as dilution products thereof.

By the same manipulative steps discussed above, virus present in products of normal or cancerous cells can be inactivated while retaining labile protein activity in such products. For instance, by the same di- or trialkylphosphate treatment one can inactivate products produced using normal or cancer cells, the exudate from normal or cancerous cells, hybridomas and products produced by gene splicing. Such treatment does not substantially adversely affect the desired protein. Cells used for production of desired protein can, of course, be mammalian as well as non-mammalian cells.

Factor VIII and factor IX coagulant activities are assayed by determining the degree of correction in APTT time of factor VIII—and factor IX—deficient plasma, respectively. J. G. Lenahan, Phillips and Phillips, *Clin. Chem.*, Vol. 12, page 269 (1966).

The activity of proteins which are enzymes is determined by measuring their enzymatic activity. Factor IX's activity can be measured by that technique.

Binding proteins can have their activities measured by determining their kinetics and affinity of binding to their natural substrates.

Lymphokine activity is measured biologically in cell systems, typically by assaying their biological activity in cell cultures.

Protein activity generally is determined by the known and standard modes for determining the activity of the protein or type of protein involved.

In order to more fully illustrate the nature of the invention and the manner of practicing the same, the following non-limiting examples are presented:

EXAMPLE 1

AHF solutions were incubated with 0.1% TNPB plus 1% Tween 80 for 18 hours at 4° C. These solutions were initially contacted with VSV virus, Sindbis virus and Sendai virus and thereafter brought in contact with an aqueous solution containing 0.1 weight percent of tri(n-butyl) phosphate (TNBP) and 1.0 weight percent detergent (Tween 80), with the following resultant virus inactivations: 4.7 logs of vesicular stomatitis virus (VSV), 5.8 logs of Sindbis virus, and 5.0 logs of Sendai virus. The virus was added just prior to the addition of the TNBP-Tween 80. The yield of AHF (labile protein/total protein) was found to be 86%.

Controls in which TNBP and Tween 80 were omitted showed little if any viral inactivation.

The results for Example 1 are shown below in Table I:

TABLE I

| Temper-ature | Time (Hrs) | AHF U/mL | AHF % Yld | Log Titer Virus VSV | Log Titer Virus Sindbis | Log Titer Virus Sendai |
|---|---|---|---|---|---|---|
| 4° C. | Start | 10.4 | (100) | 4.7 | 5.8 | 5.0 |
|  | 3 | — | — | 0.9 | −0.4 | 2.2 |
|  | 6 | — | — | 0.6 | −0.5 | 1.5 |
|  | 18 | 8.9 | 86 | <−0.5 | 0.5 | −0.5 |

Figure 2:
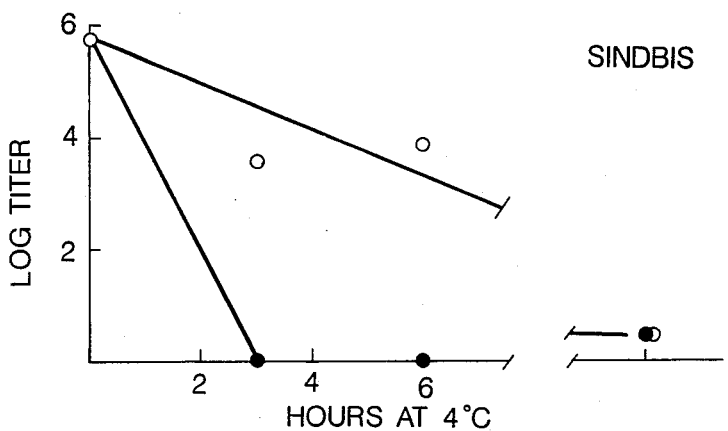
FIG. 2 shows virus inactivation as a function of log titer value versus time for Sindbis virus treated according to the present invention and treated with ether/Tween 80.
Figure 3:
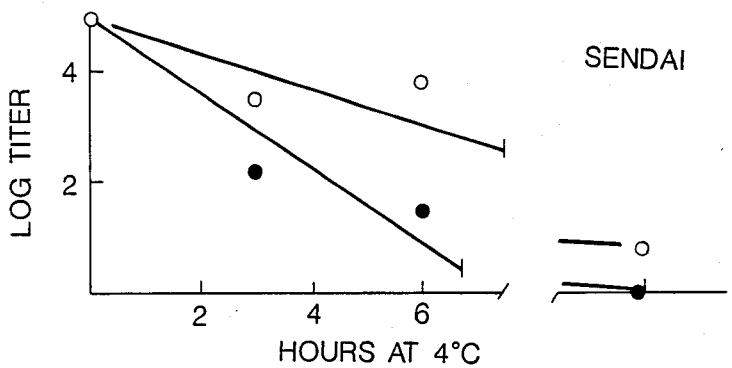
FIG. 3 shows virus inactivation as a function of log titer value versus time for Sendai virus treated according to the present invention and treated with ether/Tween 80.
Figure 4:
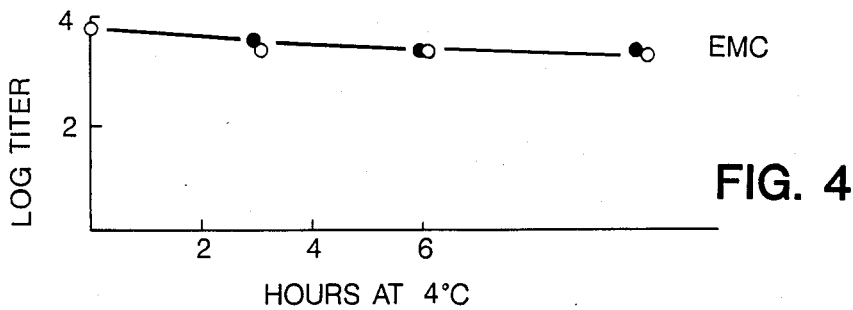
FIG. 4 shows virus inactivation as a function of log titer value versus time for EMC virus (a non-lipid coated virus) treated according to the present invention and treated with ether/Tween 80.

In FIG. 1, FIG. 2, and FIG. 3, the results of Example 1 are plotted and compared to virus inactivation with ether (20%)/Tween 80 (1%). It is seen that for VSV (FIG. 1). Sindbis (FIG. 2) and Sendai (FIG. 3), inactivation was greater (lower log titer value) for treatment according to the present invention (with TNBP) than with ether/Tween 80 treatment.

In Table II, the effect of a "Tween 80" alone in the inactivation of viruses is shown. The data shows that little if any inactivation is due to "Tween 80".

TABLE II

EFFECT OF TWEEN 80 (1%) ALONE ON VIRUS INACTIVATION

| Experiment | Temper-ature (°C.) | Duration (Hrs) | Inactivation (log#) VSV | Sindbis | Sendai | EMC |
|---|---|---|---|---|---|---|
| 1 | 0° C. | 3 | 0.3 | 0.0 | 0.0 | 0.4 |
| 2 | 0° C. | 18 | ND* | −0.1 | 0.7 | 0.5 |
|  | 22° C. | 18 | ND* | −0.1 | −0.3 | 0.0 | log titer control minus log titer treated
*not done

EXAMPLE 2

Example 1 was repeated, but at 22° C. The results for Example 2 are summarized below in Table III:

TABLE III

| Temper-ature | Time (Hrs) | AHF U/mL | AHF % Yld | Log Titer Virus VSV | Log Titer Virus Sindbis | Log Titer Virus Sendai |
|---|---|---|---|---|---|---|
| 22° C. | Un-treated | 8.3 | (100) | 4.4 | 5.1 | 5.0 |
|  | 3 | 8.2 | 99 | <−0.4 | <−0.5 | 1.8 |

The present invention may be embodied in other specific forms without departing from the spirit or essential attributes thereof and, accordingly, reference should be had to the appended claims, rather than to the foregoing specification, an indicating the scope of the invention.

We claim:

1. A process for rendering a blood product which comprises a labile blood protein substantially free of lipid-containing viruses without incurring substantial protein denaturation which comprises contacting said blood product with an effective amount of a di- or trialkylphosphate for a period of time sufficient to render said blood product substantially free of lipid-containing viruses without incurring substantial protein denaturation.

2. A process according to claim 1 wherein di- or trialkylphosphate has alkyl groups which contain 1 to 10 carbon atoms.

3. A process according to claim 2 wherein said trialkylphosphate has alkyl groups which contain 2 to 10 carbon atoms.

4. A process according to claim 2 wherein said trialkylphosphate is tri-n-butyl phosphate.

5. A process according to claim 1 wherein said contacting is conducted in the presence of a wetting agent.

6. A process according to claim 5 wherein said wetting agent is a non-ionic detergent.

7. A process according to claim 5 wherein said wetting agent is added to said blood product prior to contacting said blood product with said di- or trialkylphosphate.

8. A process according to claim 5 wherein said wetting agent is added simultaneously with said di- or trialkylphosphate to said blood product.

9. A process according to claim 5 wherein said wetting agent is added after said di- or trialkylphosphate contacts said blood product.

10. A process according to claim 6 wherein said detergent is a partial ester of sorbitol anhydrides.

11. A process according to claim 1 further comprising conducting said contacting in the presence of lipid coated virus inactivating agent selected from the group consisting of ethers and alcohols.

12. A process according to claim 5 further comprising conducting said contacting in the presence of an inactivating agent selected from the group consisting of ethers and alcohols.

13. A process according to claim 1 wherein said blood protein is selected from the group consisting of whole blood, blood plasma, red blood cells, leucocytes, platelet concentrates, a plasma concentrate, a precipitate from any fractionation of such plasma, a supernatant from any fractionation of said plasma, a serum, a cryoprecipitate, a cell lysate and proteins induced in blood cells.

14. A process according to claim 1 wherein said labile blood protein is selected from the group consisting of fibrinogen, cold insoluble globulin, properdin, IgG, IgM, IgA, betaliproprotein, plasmin-inhibitor, factor V, thrombin, antithrombin, isoagglutinins, cerutoplasmin, alpha$_1$-lipoprotein, peptidase, transferrin, thyroxine binding globulin, serum esterase, alkaline phosphates, alpha$_1$-acid glycoprotein, factor II, factor VII, factor VIII, factor IX, factor X, factor XIII, factor I, immunoglobulins, prealbumin, retinol-binding protein, albumin, alpha-globulins, beta-globulins, gamma-globulins, factor III, the complement components, fibronectin, antithrombin III, hemoglobin, interferon, T-cell growth factor and plasminogen activator.

15. A process according to claim 1 wherein following said contacting with said di- or trialkylphosphate, said di- or trialkylphosphate is removed.

16. A process according to claim 1 wherein said period of time is between about 1 minute and about 30 hours.

17. A process according to claim 1 wherein said contacting is conducted at a temperature of between about 0° C. and about 70° C.

18. A process according to claim 1 wherein said di- or trialkylphosphate is present in an amount between about 0.001% and about 1%.

19. A process according to claim 13 wherein said blood product comprises factor VIII.

20. A process according to claim 13 wherein said blood product comprises factor IX.

21. A process according to claim 1 wherein said blood product is additionally heated for at least 5 hours at 50° to 70° C.

22. A process according to claim 22 wherein the composition which is heated comprises a protein stabilizer which stabilizes a protein against denaturation by heat.

23. A process according to claim 1 wherein said labile blood protein is factor VIII.

24. A process according to claim 1 wherein said labile blood protein is factor VII.

25. A process according to claim 1 wherein said labile blood protein is factor IX.

26. A process according to claim 1 wherein said labile blood protein is factor X.

27. A process according to claim 1 wherein said labile blood protein is fibrinogen.

28. A process according to claim 1 wherein said labile blood protein is fibronectin.

29. A process according to claim 1 wherein said labile blood protein comprises an antibody against infectious hepatitis.

30. A process according to claim 1 wherein said labile blood protein is factor XIII.

31. A process according to claim 1 wherein said labile blood protein is T-cell growth factor.

32. A process according to claim 1 wherein said labile blood protein is a protein of a leucocyte.

33. A process according to claim 1 wherein said labile blood protein is a protein of a red blood cell.

34. A process according to claim 1 wherein said labile blood protein is a protein of a blood platelet concentrate.

* * * * *

UNITED STATES PATENT AND TRADEMARK OFFICE
CERTIFICATE OF CORRECTION

PATENT NO. : 4,540,573

DATED : September 10, 1985

INVENTOR(S) : Alexander R. Neurath, et al.

It is certified that error appears in the above-identified patent and that said Letters Patent are hereby corrected as shown below:

Col. 14, line 14          Delete "claim 22" and substitute --claim 21--

Signed and Sealed this

Fifteenth Day of September, 1987

*Attest:*

DONALD J. QUIGG

*Attesting Officer*     *Commissioner of Patents and Trademarks*

UNITED STATES PATENT AND TRADEMARK OFFICE
CERTIFICATE OF CORRECTION

PATENT NO. : 4,540,573
DATED : September 10, 1985
INVENTOR(S) : Alexander R. Neurath, et al It is certified that error appears in the above-identified patent and that said Letters Patent is hereby corrected as shown below:

FIG. 6 and FIG. 7    Delete "TNBP/TWEEN 80-°C" and substitute --TNBP/TWEEN 80-0°C--

Sheet 2 of Drawings    Bottom of page delete "TNBP/TWEEN 80-°C" and substitute --TNBP/TWEEN 80-0°C--

Signed and Sealed this

Eleventh Day of April, 1989

Attest:

DONALD J. QUIGG

Attesting Officer

Commissioner of Patents and Trademarks